United States Patent
Burnier et al.

(10) Patent No.: US 7,569,567 B2
(45) Date of Patent: Aug. 4, 2009

(54) 3-HETEROARYL-3,5-DIHYDRO-4-OXO-4H-PYRIDAZINO[4,5-B]INDOLE-1-CARBOXAMIDE DERIVATIVES, THEIR PREPARATION AND THERAPEUTIC USE

(75) Inventors: Philippe Burnier, Maisons-Laffitte (FR); Jacques Froissant, Brevainville (FR); Benoit Marabout, Massy (FR); Frank Marguet, Verrieres-le-Buisson (FR); Frederic Puech, La Celle Saint Cloud (FR)

(73) Assignee: sanofi-aventis, Paris (FR)

( * ) Notice: Subject to any disclaimer, the term of this patent is extended or adjusted under 35 U.S.C. 154(b) by 0 days.

(21) Appl. No.: 12/140,608

(22) Filed: Jun. 17, 2008

(65) Prior Publication Data
US 2008/0249098 A1 Oct. 9, 2008

Related U.S. Application Data

(60) Division of application No. 11/427,508, filed on Jun. 29, 2006, now Pat. No. 7,402,682, which is a continuation of application No. 10/499,725, filed as application No. PCT/FR02/03979 on Nov. 20, 2002, now Pat. No. 7,109,194.

(30) Foreign Application Priority Data
Dec. 21, 2001 (FR) ................................. 01 16701

(51) Int. Cl.
*A61K 31/503* (2006.01)
*C07D 487/02* (2006.01)
(52) U.S. Cl. .................. 514/248; 544/115; 544/234
(58) Field of Classification Search ................. 514/248, 514/250
See application file for complete search history.

(56) References Cited

U.S. PATENT DOCUMENTS 6,075,021 A 6/2000 Evanno et al.
6,451,795 B1 9/2002 Marguet et al.

FOREIGN PATENT DOCUMENTS

WO    WO 98/15552    4/1998
WO    WO 00/44751    8/2000
WO    WO 02/08229    1/2002

OTHER PUBLICATIONS

Lacapere et al. Steriods 68 (2003) 569-585.*
Lacapere, J.J., et. al., Peripheral-type benzodiazepine receptor: structure and function of a cholesterol-binding protein in steroid and bile acid biosynthesis, Steroids (2003, pp. 569-585, vol. 68).

* cited by examiner

*Primary Examiner*—Kahsay T Habte
(74) *Attorney, Agent, or Firm*—Kelly L. Bender

(57) ABSTRACT

A subject-matter of the invention is the compounds of general formula (I)

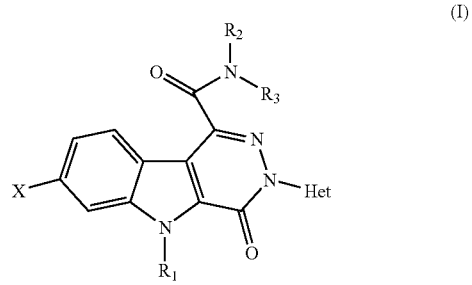

in which X represents a hydrogen or halogen atom; $R_1$ represents a hydrogen atom or a $(C_1-C_4)$alkyl group; $R_2$ and $R_3$ each represent, independently of one another, a hydrogen atom or a $(C_1-C_4)$alkyl group or else $R_2$ and $R_3$ form, with the nitrogen atom which carries them, a pyrrolidinyl, piperidinyl, morpholinyl or 4-alkylpiperazinyl group; and Het represents a heteroaromatic group of pyridinyl, 1-oxidopyridinyl, quinolinyl, isoquinolinyl, pyrimidinyl, pyrazinyl or pyridazinyl type, it being possible for the heteroaromatic group to carry one or more halogen atoms and/or one or more $(C_1-C_4)$ alkyl or $(C_1-C_4)$ alkoxy groups; in the form of bases, of addition salts with acids, of solvates or of hydrates, the pharmaceutical compositions comprising them, processes for their preparation and synthetic intermediates.

19 Claims, No Drawings

3-HETEROARYL-3,5-DIHYDRO-4-OXO-4H-PYRIDAZINO[4,5-B]INDOLE-1-CARBOXAMIDE DERIVATIVES, THEIR PREPARATION AND THERAPEUTIC USE

CROSS REFERENCE TO RELATED APPLICATIONS

This application is a division of U.S. application Ser. No. 11/427,508, filed Jun. 29, 2006, now allowed, which is a continuation of U.S. application Ser. No. 10/499,725, filed Jun. 21, 2004, now U.S. Pat. No. 7,109,194 B1, issued, Sep. 19, 2006, which was the National Stage of International application No. PCT/FR2002/03,979, filed Nov. 20, 2002, all of which are incorporated herein by reference in their entirety; which claims the benefit of priority of French Patent Application No. 01/16,701, filed Dec. 21, 2001.

A subject-matter of the invention is compounds derived from 3-heteroaryl-3,5-dihydro-4-oxo-4H-pyridazino[4,5-b]indole-1-carboxamide.

Compounds derived from 3,5-dihydropyridazino-[4,5-b]indole, disclosed in the document WO-A-00/44751, are already known, which compounds have an in vitro affinity for peripheral-type benzodiazepine receptors (PBR or p sites).

There still exists a need to find and develop products exhibiting a good in vivo activity.

The invention meets this target by providing novel compounds which exhibit an in vitro and in vivo affinity for peripheral-type benzodiazepine receptors.

A first subject-matter of the invention relates to the compounds corresponding to the general formula (I) below.

Another subject-matter of the invention relates to processes for the preparation of the compounds of general formula (I).

Another subject-matter of the invention relates to compounds which can be used in particular as intermediates in the synthesis of the compounds of general formula (I).

Another subject-matter of the invention relates to the uses of the compounds of general formula (I), in particular in medicaments or in pharmaceutical compositions.

The compounds of the invention correspond to the general formula (I):

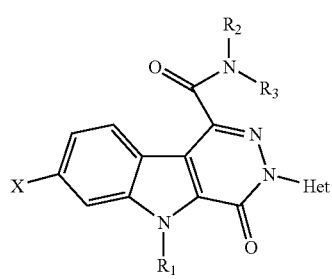

in which
X represents a hydrogen or halogen atom,
$R_1$ represents a hydrogen atom or a $(C_1-C_4)$alkyl group,
$R_2$ and $R_3$ each represent, independently of one another, a hydrogen atom or a $(C_1-C_4)$alkyl group or else $R_2$ and $R_3$ form, with the nitrogen atom which carries them, a pyrrolidinyl, piperidinyl, morpholinyl or 4-alkylpiperazinyl group, and
Het represents a heteroaromatic group of pyridinyl, 1-oxidopyridinyl, quinolinyl, isoquinolinyl, pyrimidinyl, pyrazinyl or pyridazinyl type, it being possible for the heteroaromatic group to carry one or more halogen atoms and/or one or more $(C_1-C_4)$alkyl or $(C_1-C_4)$alkoxy groups.

In the context of the present invention:
a $(C_1-C_4)$alkyl group represents a saturated and linear or branched aliphatic group comprising 1 to 4 carbon atoms. Mention may be made, by way of examples, of the methyl, ethyl, propyl, isopropyl, butyl, isobutyl or tert-butyl groups.
a $(C_1-C_4)$alkoxy group represents an oxygen radical substituted by an alkyl group comprising from 1 to 4 carbon atoms as defined above.

Preferred compounds according to the invention are the compounds for which
X represents a halogen atom; and/or
$R_1$ represents a $(C_1-C_4)$alkyl; and/or
$R_2$ and $R_3$ each represent, independently of one another, a hydrogen atom or a $(C_1-C_4)$alkyl group, more particularly a methyl or an ethyl, or else $R_2$ and $R_3$ form, with the nitrogen atom which carries them, a pyrrolidinyl, piperidinyl, morpholinyl or 4-alkylpiperazinyl group; and/or
Het represents a heteroaromatic group of pyridinyl, quinolinyl, isoquinolinyl, pyrimidinyl, pyrazinyl or pyridazinyl type which can carry one or more halogen atoms, more particularly a bromine atom, and/or one or more $(C_1-C_4)$ alkyl groups, more particularly a methyl, or $(C_1-C_4)$alkoxy groups, more particularly a methoxy.

Compounds for which X, $R_1$, $R_2$, $R_3$ and Het simultaneously are as defined above in the subgroups of preferred compounds are particularly preferred and more specifically, among these, the compounds for which:

X represents a chlorine atom and $R_1$ represents a methyl group.

By way of example, compounds of the invention are the following:
1: 7-fluoro-N,N,5-trimethyl-4-oxo-3-(pyridin-2-yl)-3,5-dihydro-4H-pyridazino[4,5-b]indole-1-carboxamide
2: 7-fluoro-N,N,5-trimethyl-4-oxo-3-(pyridin-3-yl)-3,5-dihydro-4H-pyridazino[4,5-b]indole-1-carboxamide
3: 7-fluoro-N,N,5-trimethyl-4-oxo-3-(pyridin-4-yl)-3,5-dihydro-4H-pyridazino[4,5-b]indole-1-carboxamide hydrochloride (1:1)
4: 7-fluoro-N,N,5-trimethyl-4-oxo-3-(2-methoxypyridin-5-yl)-3,5-dihydro-4H-pyridazino[4,5-b]indole-1-carboxamide
5: 7-fluoro-N,N,5-trimethyl-4-oxo-3-(quinolin-3-yl)-3,5-dihydro-4H-pyridazino[4,5-b]indole-1-carboxamide
6: 1-[[7-fluoro-5-methyl-3-(pyrimidin-2-yl)-4-oxo-3,5-dihydro-4H-pyridazino[4,5-b]indol-1-yl]carbonyl]-pyrrolidine
7: 4-methyl-1-[[7-fluoro-5-methyl-3-(pyridin-3-yl)-4-oxo-3,5-dihydro-4H-pyridazino[4,5-b]indol-1-yl]carbonyl]piperazine hydrochloride (1:1)
8: 1-[[7-fluoro-5-methyl-3-(pyridin-3-yl)-4-oxo-3,5-dihydro-4H-pyridazino[4,5-b]indol-1-yl]carbonyl]-pyrrolidine
9: 7-fluoro-N,5-dimethyl-4-oxo-3-(pyridin-3-yl)-3,5-dihydro-4H-pyridazino[4,5-b]indole-1-carboxamide
10: 7-fluoro-5-methyl-4-oxo-3-(pyridin-3-yl)-3,5-dihydro-4H-pyridazino[4,5-b]indole-1-carboxamide
11: 7-chloro-N,N,5-trimethyl-4-oxo-3-(pyridin-2-yl)-3,5-dihydro-4H-pyridazino[4,5-b]indole-1-carboxamide
12: 7-chloro-N,N,5-trimethyl-4-oxo-3-(pyridin-3-yl)-3,5-dihydro-4H-pyridazino[4,5-b]indole-1-carboxamide hydrochloride (1:1)

13: 7-chloro-N,N,5-trimethyl-4-oxo-3-(pyridin-4-yl)-3,5-dihydro-4H-pyridazino[4,5-b]indole-1-carboxamide
14: 7-chloro-N,N,5-trimethyl-4-oxo-3-(pyridin-4-yl)-3,5-dihydro-4H-pyridazino[4,5-b]indole-1-carboxamide hydrochloride (1:1)
15: 7-chloro-N,N,5-trimethyl-4-oxo-3-(5-methylpyridin-2-yl)-3,5-dihydro-4H-pyridazino[4,5-b]indole-1-carboxamide
16: 7-chloro-N,N,5-trimethyl-4-oxo-3-(2-methoxypyridin-5-yl)-3,5-dihydro-4H-pyridazino[4,5-b]indole-1-carboxamide
17: 7-chloro-N,N,5-trimethyl-4-oxo-3-(2-methylpyridin-5-yl)-3,5-dihydro-4H-pyridazino[4,5-b]indole-1-carboxamide
18: 7-chloro-N,N,5-trimethyl-4-oxo-3-(2-bromopyridin-5-yl)-3,5-dihydro-4H-pyridazino[4,5-b]indole-1-carboxamide
19: 7-chloro-N,N,5-trimethyl-4-oxo-3-(quinolin-3-yl)-3,5-dihydro-4H-pyridazino[4,5-b]indole-1-carboxamide
20: 7-chloro-N,N,5-trimethyl-4-oxo-3-(isoquinolin-4-yl)-3,5-dihydro-4H-pyridazino[4,5-b]indole-1-carboxamide
21: 7-chloro-N,N,5-trimethyl-4-oxo-3-(6-methyl-pyridazin-3-yl)-3,5-dihydro-4H-pyridazino[4,5-b]indole-1-carboxamide
22: 7-chloro-N,N,5-trimethyl-4-oxo-3-(pyrimidin-5-yl)-3,5-dihydro-4H-pyridazino[4,5-b]indole-1-carboxamide
23: 7-chloro-N,N,5-trimethyl-4-oxo-3-(pyrimidin-2-yl)-3,5-dihydro-4H-pyridazino[4,5-b]indole-1-carboxamide
24: 7-chloro-N,N,5-trimethyl-4-oxo-3-(pyrazin-2-yl)-3,5-dihydro-4H-pyridazino[4,5-b]indole-1-carboxamide
25: 1-[[7-chloro-5-methyl-3-(pyridin-3-yl)-4-oxo-3,5-dihydro-4H-pyridazino[4,5-b]indol-1-yl]carbonyl]-pyrrolidine hydrochloride (1:1)
26: 4-methyl-1-[[7-chloro-5-methyl-3-(pyridin-3-yl)-4-oxo-3,5-dihydro-4H-pyridazino[4,5-b]indol-1-yl]carbonyl] piperazine hydrochloride (1:1)
27: 1-[[7-chloro-5-methyl-3-(pyridin-4-yl)-4-oxo-3,5-dihydro-4H-pyridazino[4,5-b]indol-1-yl]carbonyl]-pyrrolidine
28: 7-chloro-N,5-dimethyl-4-oxo-3-(pyridin-4-yl)-3,5-dihydro-4H-pyridazino[4,5-b]indole-1-carboxamide
29: 7-chloro-5-methyl-4-oxo-3-(pyridin-4-yl)-3,5-dihydro-4H-pyridazino[4,5-b]indole-1-carboxamide
30: 7-chloro-N,N,5-trimethyl-4-oxo-3-(4-methoxypyridin-2-yl)-3,5-dihydro-4H-pyridazino[4,5-b]indole-1-carboxamide
31: 1-[[7-chloro-5-methyl-3-(pyridin-4-yl)-4-oxo-3,5-dihydro-4H-pyridazino[4,5-b]indol-1-yl]carbonyl]morpholine
32: 7-chloro-N,N,-diethyl-5-methyl-4-oxo-3-(pyridin-4-yl)-3,5-dihydro-4H-pyridazino[4,5-b]indole-1-carboxamide
33: 7-chloro-N-ethyl-N,5-dimethyl-4-oxo-3-(pyridin-4-yl)-3,5-dihydro-4H-pyridazino[4,5-b]indole-1-carboxamide
34: 1-[[7-chloro-5-methyl-3-(pyridin-4-yl)-4-oxo-3,5-dihydro-4H-pyridazino[4,5-b]indol-1-yl]carbonyl]-piperidine
35: 7-chloro-N,N,5-trimethyl-4-oxo-3-(2-methylpyridin-4-yl)-3,5-dihydro-4H-pyridazino[4,5-b]indole-1-carboxamide
36: 1-[[7-chloro-5-methyl-3-(2-methylpyridin-4-yl)-4-oxo-3,5-dihydro-4H-pyridazino[4,5-b]indol-1-yl]carbonyl] pyrrolidine
37: 7-chloro-N,N,5-trimethyl-3-(1-oxidopyridin-4-yl)-4-oxo-3,5-dihydro-4H-pyridazino[4,5-b]indole-1-carboxamide
38: 7-chloro-3-(2-methoxypyridin-4-yl)-N,N,5-trimethyl-4-oxo-3,5-dihydro-4H-pyridazino[4,5-b]indole-1-carboxamide
39: 3-(2-bromopyridin-4-yl)-7-chloro-N,N,5-trimethyl-4-oxo-3,5-dihydro-4H-pyridazino[4,5-b]indole-1-carboxamide The compounds of the invention can exist in the form of bases, of addition salts with acids, of solvates or of hydrates.

The compounds of general formula (I) can be prepared by the processes illustrated subsequently.

Throughout the continuation of the description, the intermediate compounds (II), (III), (IV) and (V) are those presented in the scheme below.

According to a first preparation route, a compound of general formula (II), in which X and $R_1$ are as defined above and R' and R" each represent, independently of one another, a $(C_1-C_4)$alkyl group, is treated with a heteroarylhydrazine in a polar solvent in the presence of acid at the reflux temperature, in order to obtain an ester of general formula (III) in which X, $R_1$, Het and R" are as defined above.

This ester is converted to the amide of general formula (I) by reaction with an amine of general formula $HNR_2R_3$, in which $R_2$ and $R_3$ are as defined above, for example in the presence of a trialkylaluminum derivative in a solvent such as toluene, or else by saponification of the ester of general formula (III) to the acid, using, for example, lithium hydroxide in a mixture of methanol, water and an ethereal solvent, and then by coupling the acid obtained, according to methods known to a person skilled in the art, with an amine of general formula $HNR_2R_3$ as defined above.

According to a second preparation route, a diester of general formula (II) is treated with hydrazine by heating in a solvent, such as acetic acid or toluene, in the presence of acid, in order to obtain an ester of general formula (IV) in which X, $R_1$ and R" are as defined above.

Scheme

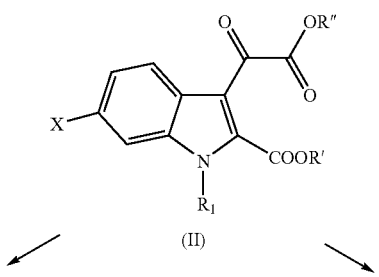

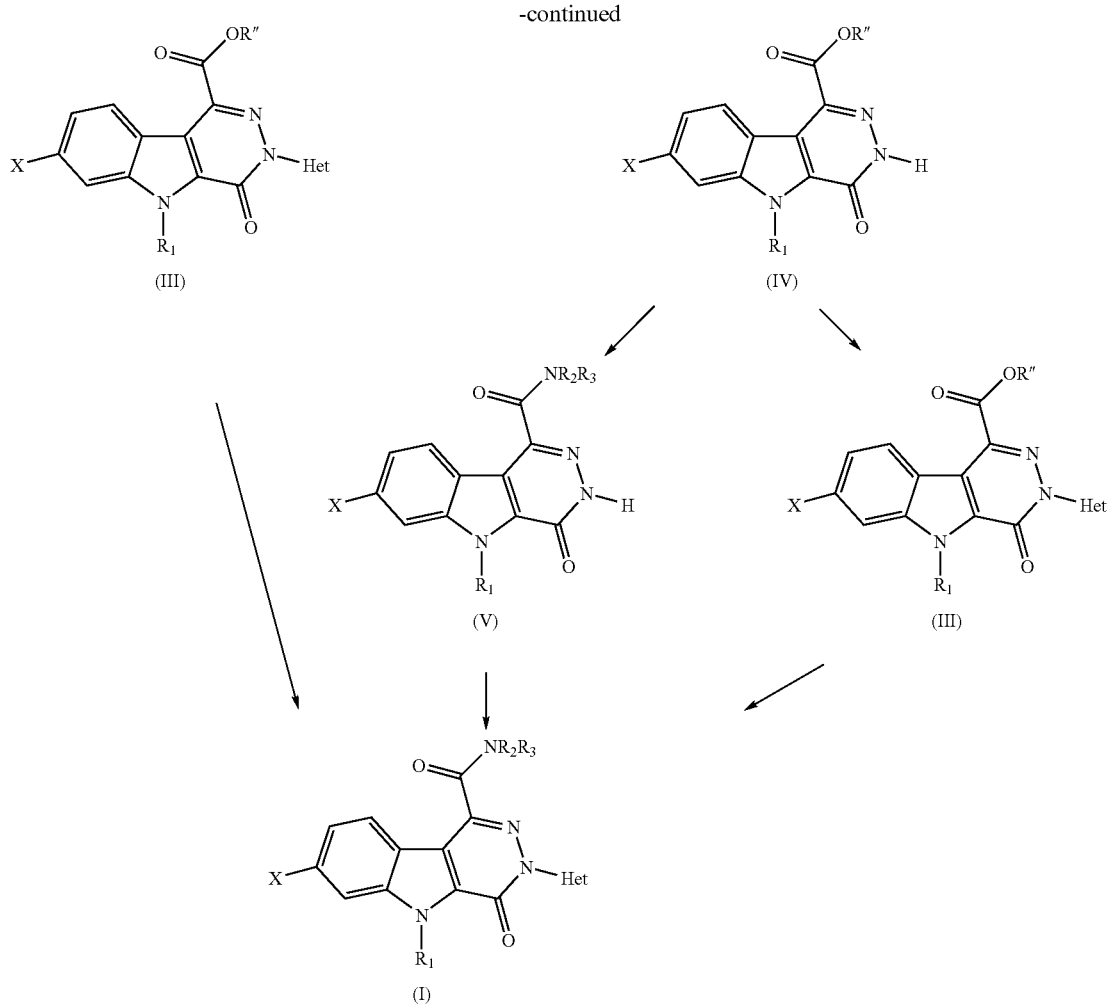

This ester is converted to the amide of general formula (V), in which X, $R_1$, $R_2$ and $R_3$ are as defined above, by reaction with an amine of general formula $HNR_2R_3$, in which $R_2$ and $R_3$ are as defined above, for example in the presence of a trialkylaluminum derivative in a solvent such as toluene.

Finally, an N-heteroarylation is carried out by a coupling reaction in the presence of a heteroaryl halide or else of a heteroarylboronic acid derivative and of a metal salt, such as a copper salt, resulting in a compound of general formula (I).

This N-heteroarylation reaction can also be carried out on the compound of general formula (IV) to result in the ester of general formula (III). This ester is finally converted to the amide of general formula (I) by reaction with an amine of general formula $HNR_2R_3$, in which $R_2$ and $R_3$ are as defined above, for example in a mixture of solvents, such as, in particular, dichloromethane and methanol.

The amides of general formulae (V) and (I) can also be obtained by saponification of the esters of respective general formulae (IV) and (III) to the acids and by then coupling the acids obtained with an amine of general formula $HNR_2R_3$, as defined above, according to methods known to a person skilled in the art.

The boronic acid derivatives carrying a heteroaromatic group are commercially available or can be prepared by methods analogous to those known in the literature (*Synth. Commun.*, 1996, 26, 3543 and Li et al., *J. Med. Chem.*, 1995, 38, 4570).

The compounds of general formula (I) for which X, $R_1$, $R_2$ and $R_3$ are as defined above and for which Het represents a heteroaromatic group of 1-oxidopyridinyl type can be prepared by oxidation, using an oxidizing agent such as hydrogen peroxide, of the equivalent derivative for which Het represents a heteroaromatic group of pyridinyl type.

The compounds of general formula (I) for which X, $R_1$, $R_2$ and $R_3$ are as defined above and for which Het represents a heteroaromatic group of 2-halopyridinyl type can be prepared by halogenation, using a phosphorus trihalide, for example, of the equivalent derivative for which Het represents a heteroaromatic group of 1-oxidopyridinyl type.

The compounds of general formula (I) for which X, $R_1$, $R_2$ and $R_3$ are as defined above and for which Het represents a heteroaromatic group of 2-alkoxypyridinyl type can be prepared by substitution, by means of a sodium alkoxide, for example, of the equivalent derivative for which Het represents a heteroaromatic group of 2-halopyridinyl type.

The preparation of the starting compounds of general formula (II) is disclosed in the document WO-A-00/44751 in the case where X is a chlorine atom. This preparation method is employed analogously when X is a fluorine atom.

Another subject-matter of the invention relates to the compounds of general formula (II)

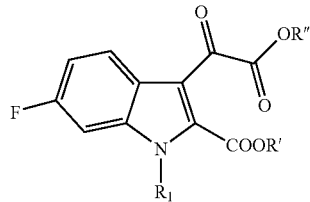

in which
R$_1$ represents a hydrogen atom or a (C$_1$-C$_4$)alkyl group,
R' and R" each represent, independently of one another, a (C$_1$-C$_4$)alkyl group, of use as synthetic intermediates in the preparation of the compounds of general formula (I).

Another subject-matter of the invention relates to the compounds of general formula (III)

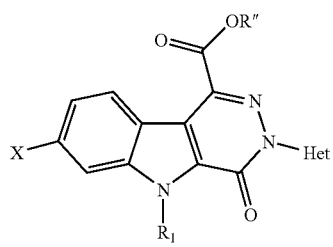

in which
X represents a hydrogen or halogen atom,
R$_1$ represents a hydrogen atom or a (C$_1$-C$_4$)alkyl group,
Het represents a heteroaromatic group of pyridinyl, quinolinyl, isoquinolinyl, pyrimidinyl, pyrazinyl or pyridazinyl type, it being possible for the heteroaromatic group to carry one or more halogen atoms and/or one or more (C$_1$-C$_4$)alkyl or (C$_1$-C$_4$)alkoxy groups,
R" represents a (C$_1$-C$_4$)alkyl group, of use as synthetic intermediates in the preparation of the compounds of general formula (I).

Another subject-matter of the invention relates to the compounds of general formula (IV)

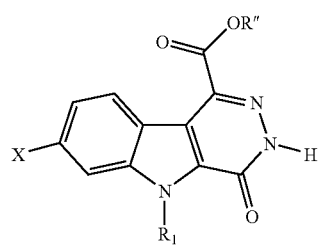

in which
X represents a hydrogen or halogen atom,
R$_1$ represents a hydrogen atom or a (C$_1$-C$_4$)alkyl group,
R" represents a (C$_1$-C$_4$)alkyl group, of use as synthetic intermediates in the preparation of the compounds of general formula (I).

Another subject-matter of the invention relates to the compounds of general formula (V)

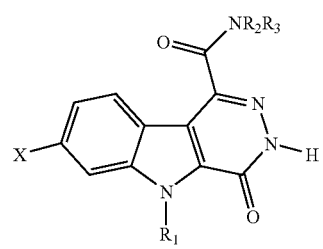

in which
X represents a hydrogen or halogen atom,
R$_1$ represents a hydrogen atom or a (C$_1$-C$_4$)alkyl group,
R$_2$ and R$_3$ each represent, independently of one another, a hydrogen atom or a (C$_1$-C$_4$)alkyl group or else R$_2$ and R$_3$ form, with the nitrogen atom which carries them, a pyrrolidinyl, piperidinyl, morpholinyl or 4-alkylpiperazinyl group,
of use as synthetic intermediates in the preparation of the compounds of general formula (I).

Other compounds are novel and of use as synthetic intermediates in the preparation of the compounds of general formula (I). They are the compounds of general formulae (III) and (IV) above in which R" no longer represents a (C$_1$-C$_4$) alkyl group but a hydrogen atom.

The examples which follow illustrate the preparation of some compounds of the invention. The elemental microanalyses and the IR and NMR spectra confirm the structures of the compounds obtained.

EXAMPLE 1

Compound No. 1

7-Fluoro-N,N,5-trimethyl-4-oxo-3-(pyridin-2-yl)-3,5-dihydro-4H-pyridazino[4,5-b]indole-1-carboxamide 1.1. Potassium 2-(4-fluoro-2-nitrophenyl)-1-methoxy-carbonylethenolate 47 g (0.419 mol) of potassium t-butoxide are introduced into 900 ml of tetrahydrofuran. The reaction medium is cooled to approximately −5° C. and 90 ml of methanol are added. 61.2 g (0.419 mol) of ethyl oxalate are subsequently introduced. A solution of 54 g (0.348 mol) of 4-fluoro-2-nitrotoluene in 100 ml of tetrahydrofuran is then added dropwise at low temperature. Stirring is maintained for 12 h at ambient temperature. The solution is filtered. The solid obtained is washed with diethyl ether and dried under reduced pressure.

78 g of a purple solid formed of potassium 2-(4-fluoro-2-nitrophenyl)-1-methoxycarbonylethenolate are obtained, comprising from 10 to 20% of potassium 2-(4-fluoro-2-nitrophenyl)-1-ethoxycarbonylethenolate.

1.2. Methyl 6-fluoro-1H-indole-2-carboxylate

A mixture of 35 g of potassium salt obtained in stage 1.1. in 500 ml of ethanol is cooled to approximately 0° C. 80 ml of concentrated hydrochloric acid are added in small portions. 35 g (627 mmol) of iron powder are also added portionwise. The mixture is heated at reflux for 5 h and then cooled and filtered. The solid obtained is rinsed with dichloromethane. The filtrate is concentrated under reduced pressure. The residue is purified by chromatography on a column of silica gel with a mixture of solvents (dichloromethane/ethyl acetate: 100/0 to 70/30). The chromatography fractions are partially concentrated. The solid which precipitates is collected by filtration, washed with cyclohexane and dried under reduced pressure.

18 g of a white solid formed of methyl 6-fluoro-1H-indole-2-carboxylate are obtained, comprising 10 to 20% of ethyl 6-fluoro-1H-indole-2-carboxylate.

1.3. Methyl 6-fluoro-1-methyl-1H-indole-2-carboxylate

A suspension of 7.9 g (197 mmol) of 60% sodium hydride and of 36.1 g (176 mmol) of methyl 6-fluoro-1H-indole-2-carboxylate (obtained in stage 1.2.) in 250 ml of N,N-dimethylformamide is stirred for 2 h at ambient temperature. 12 ml (193 mmol) of iodomethane in 50 ml of N,N-dimethylformamide are subsequently added. The mixture is stirred at ambient temperature for 12 h.

The above reaction medium is poured into a mixture of water and ice. Dichloromethane is added and the aqueous phase is neutralized with hydrochloric acid (1M). The organic phase is separated by settling, washed with water, dried over sodium sulfate, filtered and concentrated under reduced pressure. The residue is purified by chromatography on a column of silica gel with a mixture of solvents (cyclohexane/dichloromethane: 50/50; then dichloromethane/ethyl acetate: 100/0 to 70/30).

37.2 g (170 mmol) of a white compound formed of methyl 6-fluoro-1-methyl-1H-indole-2-carboxylate are isolated, comprising 10 to 20% of ethyl 6-fluoro-1-methyl-1H-indole-2-carboxylate.

1.4. Ethyl 6-fluoro-2-(methoxycarbonyl)-1-methyl-α-oxo-1H-indole-3-acetate

A solution of 6.7 ml (60 mmol) of ethyl chlorooxoacetate in 220 ml of 1,2-dichloroethane is cooled to 0° C. 6.6 ml (60 mmol) of titanium tetrachloride are added in small portions. The reaction medium is stirred for 30 min at 0° C. 10 g (47 mmol) of methyl 6-fluoro-1-methyl-1H-indole-2-carboxylate (obtained in stage 1.3.) are added. Stirring is maintained for 12 h at ambient temperature. The mixture is poured into a mixture of water and ice and extracted with dichloromethane. The organic phase is separated by settling, washed with water, dried over sodium sulfate, filtered and concentrated under reduced pressure. The residue is purified by chromatography on a column of silica gel with a mixture of solvents (cyclohexane/dichloromethane: 50/50; then dichloromethane/ethyl acetate: 100/0 to 90/10). The solid is recrystallized from a mixture of dichloromethane and ethyl acetate.

12.1 g of yellowish solid formed of ethyl 6-fluoro-2-(methoxycarbonyl)-1-methyl-α-oxo-1H-indole-3-acetate are isolated, comprising 10 to 20% of ethyl 6-fluoro-2-(ethoxycarbonyl)-1-methyl-α-oxo-1H-indole-3-acetate.

Melting point: 88-91° C.

1.5. Ethyl 7-fluoro-5-methyl-4-oxo-3-(pyridin-2-yl)-3,5-dihydro-4H-pyridazino[4,5-b]indole-1-carboxylate A solution of 0.40 g (1.36 mmol) of ethyl 6-fluoro-2-(methoxycarbonyl)-1-methyl-α-oxo-1H-indole-3-acetate (obtained in stage 1.4.) in 30 ml of absolute ethanol, a few drops of glacial acetic acid and 0.60 g (5.5 mmol) of 2-pyridinylhydrazine is brought to reflux for 17 h.

The medium is cooled. The insoluble material is collected by filtration, washed with diethyl ether and purified by chromatography on a column of silica gel with a mixture of solvents (dichloromethane/ethyl acetate: 100/0 to 0/100, then ethyl acetate/methanol: 100/0 to 90/10).

A compound (0.20 g; 0.55 mmol) is isolated in the form of a yellow solid.

1.6. 7-Fluoro-N,N,5-trimethyl-4-oxo-3-(pyridin-2-yl)-3,5-dihydro-4H-pyridazino[4,5-b]indole-1-carboxamide A solution of dimethylamine hydrochloride (0.50 g; 6 mmol) in 50 ml of toluene under argon is cooled to 0° C. and then 4 ml (8 mmol) of a trimethylaluminum solution (2M in toluene) are added in small portions. Stirring is maintained for 2 h at ambient temperature. Ethyl 7-fluoro-5-methyl-4-oxo-3-(pyridin-2-yl)-3,5-dihydro-4H-pyridazino[4,5-b]indole-1-carboxylate in the solid form (0.38 g; 1.0 mmol), obtained in stage 1.5., is subsequently added and the reaction medium is heated at 110° C. for 5 h.

The solution is cooled to approximately 0° C. and water is added dropwise. Dichloromethane and then 30% sodium hydroxide are subsequently added until the aluminum derivatives have been dissolved. The organic phase is separated by settling, washed with water, dried over sodium sulfate, filtered and concentrated under reduced pressure. The residue is purified by chromatography on a column of silica gel with a mixture of solvents (dichloromethane/ethyl acetate: 90/10 to 0/100, then ethyl acetate/methanol: 100/0 to 90/10). The solid obtained is recrystallized from a mixture of dichloromethane and ethyl acetate.

0.070 g (6.5 mmol) of compound is isolated in the form of a white solid.

Melting point: 199-200° C.

EXAMPLE 2

Compound No. 12

7-Chloro-N,N,5-trimethyl-4-oxo-3-(pyridin-3-yl)-3,5-dihydro-4H-pyridazino[4,5-b]indole-1-carboxamide hydrochloride (1:1)

2.1. Ethyl 7-chloro-5-methyl-4-oxo-3,5-dihydro-4H-pyridazino[4,5-b]indole-1-carboxylate A solution of 4.38 g (13.5 mmol) of ethyl 6-chloro-2-(ethoxycarbonyl)-1-methyl-α-oxo-1H-indole-3-acetate (disclosed in WO-A-00/44751), of 65 ml of glacial acetic acid and of 2.7 ml (55.7 mmol) of hydrazine monohydrate is brought to reflux for 3 h.

The medium is cooled. An insoluble material is collected by filtration, washed with water and dried under reduced pressure.

3.58 g (11.7 mmol) of compound are isolated in the form of a white solid.

Melting point: 302-303° C.

2.2. 7-Chloro-N,N,5-trimethyl-4-oxo-3,5-dihydro-4H-pyridazino[4,5-b]indole-1-carboxamide 2.45 g (30 mmol) of dimethylamine hydrochloride in 30 ml of toluene are introduced under argon. The solution is cooled to 0° C. and then 15 ml (30 mmol) of a trimethylaluminum solution (2M in toluene) are added in small portions. The reaction medium is stirred for 2 h at ambient temperature.

30 ml (20.1 mmol) of the solution prepared above are added to a suspension of 2 g (6.5 mmol) of ethyl 7-chloro-5-methyl-4-oxo-3,5-dihydro-4H-pyridazino[4,5-b]indole-1-carboxylate (obtained in stage 2.1.) in 60 ml of toluene. The reaction medium is heated at 100° C. for 3 h.

The solution is cooled to approximately 0° C. and poured into a mixture of an aqueous hydrochloric acid solution (1M) and ice. The reaction medium is subsequently basified with an aqueous sodium hydroxide solution (1M). The precipitate obtained is filtered off, washed with water and dried under reduced pressure.

A compound (1.99 g; 6.5 mmol) is isolated in the form of a light beige solid.

Melting point: >300° C.

2.3. 7-Chloro-N,N,5-trimethyl-4-oxo-3-(pyridin-3-yl)-3,5-dihydro-4H-pyridazino[4,5-b]indole-1-carboxamide hydrochloride (1:1)

0.4 g of 7-chloro-N,N,5-trimethyl-4-oxo-3,5-dihydro-4H-pyridazino[4,5-b]indole-1-carboxamide (1.3 mmol), obtained in stage 2.2., is dissolved in 35 ml of N-methylpyrrolidone. 0.21 ml (2.6 mmol) of pyridine, 0.36 ml (2.6 mmol) of triethylamine, 340 mg of molecular sieve, 0.47 g (2.6 mmol) of cupric acetate and 0.42 g (2.6 mmol) of 2-(pyridin-3-yl)-1,3,2-dioxaborinane are introduced at ambient temperature and under an argon atmosphere. After reacting for 24 h, the insoluble materials are separated by filtration and 0.21 ml (2.6 mmol) of pyridine, 0.36 ml (2.6 mmol) of triethylamine, 340 mg of molecular sieve, 0.47 g (2.6 mmol) of cupric acetate and 0.42 g (2.6 mmol) of 2-(pyridin-3-yl)-1,3,2-dioxaborinane are added to the solution. Stirring is maintained for 24 h. The insoluble materials are separated by filtration. The solvent is removed under reduced pressure. Dichloromethane and water are added to the evaporation residue. The aqueous phase is extracted with dichloromethane. The organic phases are combined, washed with water, dried over sodium sulfate, filtered and concentrated under reduced pressure. The residue is purified by chromatography on a column of silica (eluent: heptane/ethyl acetate: 10/90). The white solid obtained is triturated in diethyl ether. 400 mg of a white solid are isolated.

The hydrochloride is formed by dissolution of the solid isolated above in ethanol and by addition of a solution of hydrochloric acid (5N) in propan-2-ol. After recrystallization from propan-2-ol, a compound (0.35 g; 0.84 mmol) is isolated in the form of a white solid.

Melting point: 228-230° C.

EXAMPLE 3

Compound No. 4

7-Fluoro-N,N,5-trimethyl-4-oxo-3-(2-methoxypyridin-5-yl)-3,5-dihydro-4H-pyridazino[4,5-b]indole-1-carboxamide

3.1. Ethyl 7-fluoro-5-methyl-4-oxo-3,5-dihydro-4H-pyridazino[4,5-b]indole-1-carboxylate A solution of 7.80 g (26.6 mmol) of ethyl 6-fluoro-2-(methoxycarbonyl)-1-methyl-α-oxo-1H-indole-3-acetate (obtained in stage 1.4. of Example 1), of 200 ml of glacial acetic acid and of 5 ml (103 mmol) of hydrazine monohydrate is heated at 90° C. for 20 h.

The medium is cooled. After addition of water, an insoluble material is collected by filtration, washed with water and dried under reduced pressure.

5.60 g (19.3 mmol) of compound are isolated in the form of a white solid.

Melting point: 314-315° C.

3.2. 7-Fluoro-N,N,5-trimethyl-4-oxo-3,5-dihydro-4H-pyridazino[4,5-b]indole-1-carboxamide A solution of 2.50 g (30.6 mmol) of dimethylamine hydrochloride in 150 ml of toluene, under argon, is cooled to 0° C. and then 18 ml (36 mmol) of a trimethylaluminum solution (2M in toluene) are added in small portions. Stirring is maintained for 2 h at ambient temperature. 2.6 g (9 mmol) of ethyl 7-fluoro-5-methyl-4-oxo-3,5-dihydro-4H-pyridazino[4,5-b]indole-1-carboxylate in the solid form (obtained in stage 3.1.) are subsequently added. The reaction medium is heated at 110° C. for 18 h.

The solution is cooled to approximately 0° C. Water and then a 1M hydrochloric acid solution are added dropwise until a pH of between 1 and 2 is obtained. The precipitate is collected by filtration, washed with water and dried under reduced pressure in the presence of phosphorus pentoxide.

A compound (1.10 g; 3.8 mmol) is isolated in the form of a white solid.

Melting point: >300° C.

3.3. 7-Fluoro-N,N,5-trimethyl-4-oxo-3-(2-methoxypyridin-5-yl)-3,5-dihydro-4H-pyridazino[4,5-b]indole-1-carboxamide A solution of 0.3 g (1.04 mmol) of 7-fluoro-N,N,5-trimethyl-4-oxo-3,5-dihydro-4H-pyridazino[4,5-b]-indole-1-carboxamide (obtained in stage 3.2.), 0.120 g (0.63 mmol) of cuprous iodide, 0.20 g (1.45 mmol) of potassium carbonate and 0.60 g (3.19 mmol) of 3-bromo-6-methoxypyridine in 50 ml of N,N-dimethylformamide is heated at 150° C. for 20 h. The reaction mixture is cooled and concentrated under reduced pressure. Dichloromethane, water and a sodium hydroxide solution (1M) are added. The organic phase is separated by settling, washed with water, dried over sodium sulfate, filtered and concentrated under reduced pressure. The residue is purified by chromatography on a column of silica gel (eluent: dichloromethane/ethyl acetate: 100/0 to 0/100; then ethyl acetate/methanol:95/5). The white solid obtained is recrystallized from a dichloromethane/ethyl acetate mixture and washed with diethyl ether. A white solid (0.26 g; 0.66 mmol) is isolated.

Melting point: 225-226° C.

EXAMPLE 4

Compound No. 9

7-Fluoro-N,5-dimethyl-4-oxo-3-(pyridin-3-yl)-3,5-dihydro-4H-pyridazino[4,5-b]indole-1-carboxamide

4.1. Ethyl 7-fluoro-5-methyl-4-oxo-3-(pyridin-3-yl)-3,5-dihydro-4H-pyridazino[4,5-b]indole-1-carboxylate Ethyl 7-fluoro-5-methyl-4-oxo-3,5-dihydro-4H-pyridazino[4,5-b]indole-1-carboxylate (0.9 g; 3.11 mmol), obtained in stage 3.1. of Example 3, is dissolved in 60 ml of N-methylpyrrolidone. 0.50 ml (6.2 mmol) of pyridine, 0.8 ml (5.7 mmol) of triethylamine, 4 g of molecular sieve, 1.0 g (5.5 mmol) of cupric acetate and 0.90 g (5.5 mmol) of 2-(3-pyridinyl)-1,3,2-dioxaborinane are introduced at ambient temperature and under an argon atmosphere. After reacting for 24 h, the solvent is removed under reduced pressure. Dichloromethane, water and sodium hydroxide (1M) are added. The insoluble materials are separated by filtration, the organic phase is separated by settling and the aqueous phase is extracted with dichloromethane. The organic phases are combined, washed with water, dried over sodium sulfate, filtered and concentrated under reduced pressure. The residue is purified by chromatography on a column of silica gel (eluent: dichloromethane/ethyl acetate: 100/0 to 0/100; ethyl acetate/methanol: 100/0 to 90/10).

A white solid (0.57 g) is isolated.

Melting point: 214-215° C.

4.2. 7-Fluoro-N,5-dimethyl-4-oxo-3-(pyridin-3-yl)-3,5-dihydro-4H-pyridazino[4,5-b]indole-1-carboxamide A stream of gaseous methylamine is introduced into a solution of 0.28 g (0.76 mmol) of ethyl 7-fluoro-5-methyl-4-oxo-3-(pyridin-3-yl)-3,5-dihydro-4H-pyridazino[4,5-b]indole-1-carboxylate (obtained in stage 4.1.) in 30 ml of dichloromethane and 70 ml of methanol. Stirring is maintained for 4 h. The reaction medium is concentrated under reduced pressure. The residue is purified by chromatography on a column of silica gel (eluent: dichloromethane/methanol: 100/0 to 90/10). The solid obtained is recrystallized from a mixture of dichloromethane and ethyl acetate.

A white solid (0.22 g) is isolated.

Melting point: 270-272° C.

EXAMPLE 5

Compound No. 6

1-[[7-Fluoro-5-methyl-3-(pyrimidin-2-yl)-4-oxo-3,5-dihydro-4H-pyridazino[4,5-b]indol-1-yl]carbonyl]-pyrrolidine

5.1. 1-[[7-Fluoro-5-methyl-4-oxo-3,5-dihydro-4H-pyridazino[4,5-b]indol-1-yl]carbonyl]pyrrolidine 12 ml (24 mmol) of a trimethylaluminum solution (2M in toluene) in 100 ml of toluene, under argon, are cooled to 0° C. and then 2 ml (24 mmol) of pyrrolidine are added in small portions. Stirring is maintained for 2 h at ambient temperature. 2.0 g (6.9 mmol) of ethyl 7-fluoro-5-methyl-4-oxo-3,5-dihydro-4H-pyridazino[4,5-b]indole-1-carboxylate (obtained in stage 3.1. of Example 3) in the solid form are subsequently added. The reaction medium is heated at 110° C. for 18 h.

The solution is cooled to approximately 0° C. Water and then a solution of hydrochloric acid (1M) are added dropwise until a pH of between 1 and 2 is obtained. The precipitate obtained is filtered off, washed with water and dried under reduced pressure in the presence of phosphorus pentoxide.

A compound (1.50 g; 4.6 mmol) is isolated in the form of a white solid.

Melting point: >300° C.

5.2. 1-[[7-Fluoro-5-methyl-3-(pyrimidin-2-yl)-4-oxo-3,5-dihydro-4H-pyridazino[4,5-b]indol-1-yl]carbonyl]-pyrrolidine A solution of 0.24 g (0.73 mmol) of 1-[[7-fluoro-5-methyl-4-oxo-3,5-dihydro-4H-pyridazino[4,5-b]indol-1-yl]carbonyl]pyrrolidine (obtained in stage 5.1.), 0.120 g (0.63 mmol) of cuprous iodide, 0.15 g (1.09 mmol) of potassium carbonate and of 0.30 g (1.89 mmol) of 2-bromopyrimidine in 40 ml of N,N-dimethylformamide is heated at 150° C. for 16 h. The reaction mixture is cooled and concentrated under reduced pressure. Dichloromethane, water and a concentrated sodium hydroxide solution are added. The organic phase is separated by settling, filtered through Celite®, washed with water, dried over sodium sulfate, filtered and concentrated under reduced pressure. The residue is purified by chromatography on a column of silica gel (eluent: dichloromethane/ethyl acetate: 80/20 to 0/100; ethyl acetate/methanol: 100/0 to 90/10). The solid obtained is recrystallized from a dichloromethane/ethyl acetate mixture and washed with diethyl ether.

A white solid (0.04 g; 0.10 mmol) is isolated.

Melting point: 238-239° C.

EXAMPLE 6

Compound No. 26

4-Methyl-1-[[7-chloro-5-methyl-3-(pyridin-3-yl)-4-oxo-3,5-dihydro-4H-pyridazino[4,5-b]indol-1-yl]carbonyl]-piperazine hydrochloride (1:1)

6.1. 4-Methyl-1-[[7-chloro-5-methyl-4-oxo-3,5-dihydro-4H-pyridazino[4,5-b]indol-1-yl]carbonyl]-piperazine A solution of 4-methylpiperazine (1.1 ml; 10 mmol) in 10 ml of toluene is cooled to 0° C. under argon. 5 ml (10 mmol) of a trimethylaluminum solution (2M in toluene) are added in small portions. Stirring is maintained for 2 h at ambient temperature. 1.0 g (3.27 mmol) of ethyl 7-chloro-5-methyl-4-oxo-3,5-dihydro-4H-pyridazino[4,5-b]indole-1-carboxylate (obtained in stage 2.1. of Example 2) in 30 ml of toluene is subsequently added. The reaction medium is heated at 110° C. for 2 h.

The solution is cooled to approximately 0° C. Water and then a concentrated sodium hydroxide solution are added dropwise. The precipitate is filtered off, washed with water and dried under reduced pressure in the presence of phosphorus pentoxide.

A compound (0.89 g) is isolated in the form of a white solid.

6.2. 4-Methyl-1-[[7-chloro-5-methyl-3-(pyridin-3-yl)-4-oxo-3,5-dihydro-4H-pyridazino[4,5-b]indol-1-yl]carbonyl]piperazine hydrochloride (1:1)

4-Methyl-1-[[7-chloro-5-methyl-4-oxo-3,5-dihydro-4H-pyridazino[4,5-b]indol-1-yl]carbonyl]-piperazine (0.75 g; 2.1 mmol), obtained in stage 6.1., is dissolved in 60 ml of N-methylpyrrolidone. 0.39 ml (4.8 mmol) of pyridine, 0.67 ml (4.8 mmol) of triethylamine, 800 mg of molecular sieve, 0.87 g (4.8 mmol) of cupric acetate and 0.78 g (4.8 mmol) of 2-(pyridin-3-yl)-1,3,2-dioxaborinane are introduced at ambient temperature and under an argon atmosphere. After reacting for 24 h, the insoluble materials are separated by filtration. 0.39 ml (4.8 mmol) of pyridine, 0.67 ml (4.8 mmol) of triethylamine, 2.0 g of molecular sieve, 0.87 g (4.8 mmol) of cupric acetate and 0.78 g (4.8 mmol) of 2-(pyridin-3-yl)-1,3,2-dioxaborinane are added to the solution. Stirring is extended for a further 24 h. The solvent is removed under reduced pressure. Dichloromethane and water are added. The insoluble materials are separated by filtration. The organic phase is separated by settling and the aqueous phase is extracted with dichloromethane. The organic phases are combined, washed with water, dried over sodium sulfate, filtered and concentrated under reduced pressure. The residue is triturated in diisopropyl ether. The precipitate obtained is collected by filtration and purified by chromatography on a column of silica gel (eluent: dichloromethane/methanol: 100/0 to 90/10). A cream-colored solid (0.3 g) is isolated.

The hydrochloride is formed by dissolution of the solid in propan-2-ol and by addition of 7 ml of a solution of hydrochloric acid (0.1N) in propan-2-ol. After recrystallization from propan-2-ol, a compound (0.23 g; 0.44 mmol) is isolated in the form of a white solid.

Melting point: 267-268° C. (decomposition).

EXAMPLE 7

Compound No. 11

7-Chloro-N,N,5-trimethyl-4-oxo-3-(pyridin-2-yl)-3,5-dihydro-4H-pyridazino[4,5-b]indole-1-carboxamide 0.4 g of 7-chloro-N,N,5-trimethyl-4-oxo-3,5-dihydro-4H-pyridazino[4,5-b]indole-1-carboxamide (1.3 mmol), obtained in stage 2.2. of Example 2, is dissolved in 35 ml of N-methylpyrrolidone. 0.2 ml (2.6 mmol) of pyridine, 0.36 ml (2.6 mmol) of triethylamine, 420 mg of molecular sieve, 0.48 g (2.6 mmol) of cupric acetate and 0.874 g (2.6 mmol) of a mixture [1:1] of lithium tripropoxypyridin-2-ylboronate and propanol are introduced at ambient temperature and under an argon atmosphere. After reacting for 24 h, 0.2 ml (2.6 mmol) of pyridine, 0.36 ml (2.6 mmol) of triethylamine, 420 mg of molecular sieve, 0.48 g (2.6 mmol) of cupric acetate and 0.874 g (2.6 mmol) of a mixture [1:1] of lithium tripropoxy-pyridin-2-ylboronate and propanol are added to the solution. Stirring is extended for an additional 24 h. The solvent is evaporated. Dichloromethane and water are added. The organic phase is separated by settling and the aqueous phase is extracted with dichloromethane. The organic phases are combined, dried over sodium sulfate, filtered and concentrated under reduced pressure. The residue is purified by chromatography on a column of silica gel (eluent: dichloromethane/methanol: 100/0 to 95/5). The solid obtained is recrystallized from ethanol.

A light beige solid (0.95 g) is isolated.
Melting point: 210-211° C.

EXAMPLE 8

Compound No. 14

7-Chloro-N,N,5-trimethyl-4-oxo-3-(pyridin-4-yl)-3,5-dihydro-4H-pyridazino[4,5-b]indole-1-carboxamide hydrochloride (1:1)

0.4 g of 7-chloro-N,N,5-trimethyl-4-oxo-3,5-dihydro-4H-pyridazino[4,5-b]indole-1-carboxamide (1.3 mmol), obtained in stage 2.2. of Example 2, is dissolved in 35 ml of N-methylpyrrolidone. 0.2 ml (2.6 mmol) of pyridine, 0.4 ml (2.7 mmol) of triethylamine, 300 mg of molecular sieve, 0.48 g (2.6 mmol) of cupric acetate and 0.32 g (2.6 mmol) of pyridin-4-ylboronic acid are introduced at ambient temperature and under an argon atmosphere. After reacting for 24 h, the insoluble materials are separated by filtration and 0.2 ml (2.6 mmol) of pyridine, 0.4 ml (2.7 mmol) of triethylamine, 300 mg of molecular sieve, 0.48 g (2.6 mmol) of cupric acetate and 0.32 g (2.6 mmol) of pyridin-4-ylboronic acid are added to the solution. Stirring is maintained for 24 h. The insoluble materials are separated by filtration. The solvent is removed under reduced pressure. Dichloromethane and water are added to the evaporation residue. The aqueous phase is extracted with dichloromethane. The organic phases are combined, washed with water, dried over sodium sulfate, filtered and concentrated under reduced pressure. The residue is purified by chromatography on a column of silica gel (eluent: cyclohexane/ethyl acetate: 10/90, then dichloromethane/methanol: 95/5). The white solid obtained is triturated in diethyl ether. 350 mg of 7-chloro-N,N,5-trimethyl-4-oxo-3-(pyridin-4-yl)-3,5-dihydro-4H-pyridazino[4,5-b]indole-1-carboxamide (Compound No. 13) are isolated in the form of a white solid.

Melting point: 276-278° C.

The hydrochloride is formed by dissolution of the solid isolated above in ethanol and by addition of a solution of hydrochloric acid (5N) in propan-2-ol. After recrystallization from propan-2-ol, a compound (0.30 g; 0.72 mmol) is isolated in the form of a white solid.

Melting point: 263-265° C.

EXAMPLE 9

Compound No. 37

7-Chloro-N,N,5-trimethyl-3-(oxidopyridin-4-yl)-4-oxo-3,5-dihydro-4H-pyridazino[4,5-b]indole-1-carboxamide 0.35 g (0.92 mmol) of 7-chloro-N,N,5-trimethyl-4-oxo-3-(pyridin-4-yl)-3,5-dihydro-4H-pyridazino[4,5-b]indole-1-carboxamide, obtained in Example 8, is dissolved in 30 ml of glacial acetic acid. 3.5 g (36 mmol) of a hydrogen peroxide solution (35% in water) are slowly added. The reaction mixture is heated at 80° C. for 30 h and then cooled to ambient temperature. Water and then sodium hydrogencarbonate are added until a pH of approximately 8 is obtained. The aqueous phase is extracted with dichloromethane. The organic phase is washed with water, dried over sodium sulfate, filtered and concentrated under reduced pressure. The residue is purified by chromatography on a column of silica gel (eluent: dichloromethane/methanol: 98/2 to 80/20). The solid obtained is recrystallized from methanol. 100 mg of compound are obtained in the form of a white solid.

Melting point: 301-304° C.

EXAMPLE 10

Compound No. 38

7-Chloro-3-(2-methoxypyridin-4-yl)-N,N,5-trimethyl-4-oxo-3,5-dihydro-4H-pyridazino[4,5-b]indole-1-carboxamide

10.1. 3-(2-Bromopyridin-4-yl)-7-chloro-N,N,5-trimethyl-4-oxo-3,5-dihydro-4H-pyridazino[4,5-b]indole-1-carboxamide 0.34 g (0.85 mmol) of 7-chloro-N,N,5-trimethyl-3-(1-oxidopyridin-4-yl)-4-oxo-3,5-dihydro-4H-pyridazino[4,5-b]indole-1-carboxamide, obtained in Example 9, is dissolved in 50 ml of dichloromethane under an inert atmosphere. 0.24 ml (1.7 mmol) of triethylamine is added. The mixture is cooled with a bath of ice-cold water and 0.49 g (1.7 mmol) of phosphorus oxybromide is added in small portions. The reaction medium is stirred for 30 minutes at ambient temperature, then heated for 2 h 30 at reflux and, finally, cooled to ambient temperature. It is subsequently poured onto crushed ice. Dichloromethane and an aqueous sodium hydroxide solution (1M) are added until a basic pH is reached. The organic phase is separated by settling, washed with water, dried over sodium sulfate, filtered and concentrated under reduced pressure. The residue is purified by chromatography on a column of silica gel (eluent: dichloromethane/ethyl acetate: 80/20 to 0/100). 180 mg of a white solid are isolated. This compound is used as is in the following stage.

10.2. 7-Chloro-3-(2-methoxypyridin-4-yl)-N,N,5-trimethyl-4-oxo-3,5-dihydro-4H-pyridazino[4,5-b]indole-1-carboxamide 120 mg (5.2 mmol) of sodium are added under an inert atmosphere to 20 ml of methanol. 180 mg (0.39 mmol) of 3-(2-bromopyridin-4-yl)-7-chloro-N,N,5-trimethyl-4-oxo-3,5-dihydro-4H-pyridazino[4,5-b]indole-1-carboxamide, obtained in Example 10.1., and 20 ml of N,N-dimethylformamide are added. The solution is heated at 80° C. for 14 h. It is cooled to ambient temperature and then concentrated under reduced pressure. Water and dichloromethane are added to the residue. The organic phase is separated by settling, washed with water, dried over sodium sulfate, filtered and concentrated under reduced pressure. The residue is purified by chromatography on a column of silica gel (eluent: dichloromethane/ethyl acetate: 80/20 to 0/100). The solid obtained is recrystallized from a dichloromethane/ethyl acetate mixture and then rinsed with diethyl ether. 60 mg of a white solid are isolated.

Melting point: 237-238° C.

The chemical structures and the physical properties of some compounds of the invention are illustrated in the following table.

In the "Salt" column of this table, "HCl" denotes a hydrochloride and "-" denotes a compound in the form of the base. The acid:base molar ratios are indicated opposite.

TABLE

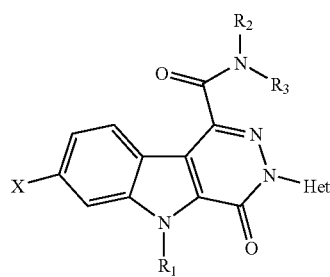

(I)

| Compound No. | X | $R_1$ | $NR_2R_3$ | Het | Salt | M.p. (° C.) |
|---|---|---|---|---|---|---|
| 1 | F | $CH_3$ | $N(CH_3)_2$ | pyridin-2-yl | — | 199-200 |
| 2 | F | $CH_3$ | $N(CH_3)_2$ | pyridin-3-yl | — | 220-221 |
| 3 | F | $CH_3$ | $N(CH_3)_2$ | pyridin-4-yl | HCl 1:1 | 266-271 |
| 4 | F | $CH_3$ | $N(CH_3)_2$ | 2-methoxypyridin-5-yl | — | 225-226 |
| 5 | F | $CH_3$ | $N(CH_3)_2$ | quinolin-3-yl | — | 237-238 |
| 6 | F | $CH_3$ | pyrrolidinyl | pyrimidin-2-yl | — | 238-239 |
| 7 | F | $CH_3$ | 4-methylpiperazinyl | pyridin-3-yl | HCl 1:1 | 269-273 |
| 8 | F | $CH_3$ | pyrrolidinyl | pyridin-3-yl | — | 220-221 |

TABLE-continued

(I)

| Compound No. | X | R₁ | NR₂R₃ | Het | Salt | M.p. (° C.) |
|---|---|---|---|---|---|---|
| 9 | F | CH₃ | NH(CH₃) | pyridin-3-yl | — | 270-272 |
| 10 | F | CH₃ | NH₂ | pyridin-3-yl | — | 319-320 |
| 11 | Cl | CH₃ | N(CH₃)₂ | pyridin-2-yl | — | 210-211 |
| 12 | Cl | CH₃ | N(CH₃)₂ | pyridin-3-yl | HCl 1:1 | 228-230 |
| 13 | Cl | CH₃ | N(CH₃)₂ | pyridin-4-yl | — | 276-278 |
| 14 | Cl | CH₃ | N(CH₃)₂ | pyridin-4-yl | HCl 1:1 | 263-265 |
| 15 | Cl | CH₃ | N(CH₃)₂ | 5-methylpyridin-2-yl | — | 222-224 |
| 16 | Cl | CH₃ | N(CH₃)₂ | 2-methoxypyridin-5-yl | — | 236-237 |
| 17 | Cl | CH₃ | N(CH₃)₂ | 2-methylpyridin-5-yl | — | 214-216 |
| 18 | Cl | CH₃ | N(CH₃)₂ | 2-bromopyridin-5-yl | — | 250-252 |
| 19 | Cl | CH₃ | N(CH₃)₂ | quinolin-3-yl | — | 271-272 |
| 20 | Cl | CH₃ | N(CH₃)₂ | isoquinolin-4-yl | — | 189-191 |
| 21 | Cl | CH₃ | N(CH₃)₂ | 6-methylpyridazin-3-yl | — | 238-239 |
| 22 | Cl | CH₃ | N(CH₃)₂ | pyrimidin-5-yl | — | 251-252 |
| 23 | Cl | CH₃ | N(CH₃)₂ | pyrimidin-2-yl | — | 272-274 |
| 24 | Cl | CH₃ | N(CH₃)₂ | pyrazin-2-yl | — | 231-232 |
| 25 | Cl | CH₃ | 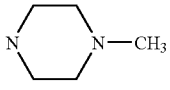 | pyridin-3-yl | HCl 1:1 | 232-234 |
| 26 | Cl | CH₃ |  | pyridin-3-yl | HCl 1:1 | 267-268 |
| 27 | Cl | CH₃ |  | pyridin-4-yl | — | 236-237 |
| 28 | Cl | CH₃ | NH(CH₃) | pyridin-4-yl | — | 321-323 |
| 29 | Cl | CH₃ | NH₂ | pyridin-4-yl | — | 341-346 |
| 30 | Cl | CH₃ | N(CH₃)₂ | 4-methoxypyridin-2-yl | — | 243-244 |
| 31 | Cl | CH₃ |  | pyridin-4-yl | — | 307-308 |
| 32 | Cl | CH₃ | N(CH₂CH₃)₂ | pyridin-4-yl | — | 217-218 |
| 33 | Cl | CH₃ | NCH₃(CH₂CH₃) | pyridin-4-yl | — | 211-213 |
| 34 | Cl | CH₃ |  | pyridin-4-yl | — | 242-243 |
| 35 | Cl | CH₃ | N(CH₃)₂ | 2-methylpyridin-4-yl | — | 267-269 |
| 36 | Cl | CH₃ |  | 2-methylpyridin-4-yl | — | 246-247 |
| 37 | Cl | CH₃ | N(CH₃)₂ | 1-oxidopyridin-4-yl | — | 301-304 |
| 38 | Cl | CH₃ | N(CH₃)₂ | 2-methoxypyridin-4-yl | — | 237-238 |

The compounds of the invention have been subjected to pharmacological tests which have demonstrated their advantage as substances with therapeutic activities.

The compounds of the invention also exhibit characteristics of solubility in water which promote good in vivo activity.

Study of the Binding of [$^3$H]Ro5-4864 to Peripheral-Type Benzodiazepine Receptors (PBR or p Sites)

The affinity of the compounds of the invention for PBR or p sites (sites of binding of peripheral type to benzodiazepines) was determined.

The p site receptors can be labeled selectively in rat kidney membranes incubated in the presence of [$^3$H]Ro5-4864. The compounds of the invention have formed the subject of an in vitro study with respect to their affinity for these receptors.

The animals used are male Sprague-Dawley rats (Iffa Credo) weighing 180 to 300 g. After decapitation, the kidney is removed and the tissue is homogenized at 4° C. using a Polytron™ homogenizer for 2 min at 6/10 of the maximum speed in 35 volumes of 50 mM $Na_2HPO_4$ phosphate buffer at a pH adjusted to 7.5 with $NaH_2PO_4$. The membrane homogenate is filtered through gauze and diluted tenfold with buffer.

[$^3$H]Ro5-4864 (specific activity: 70-90 Ci/mmol; New England Nuclear), at a concentration of 0.5 nM, is incubated in the presence of 100 µl of the membrane homogenate in a final volume of 1 ml of buffer comprising the test compound.

After incubating for 3 h at 0° C., the membranes are recovered by filtration through Whatman GF/B™ filters washed with 2 times 4.5 ml of cold (0° C.) incubation buffer. The amount of radioactivity retained by the filter is measured by liquid scintigraphy.

For each concentration of studied compound, the percentage of inhibition of the binding of [$^3$H]Ro5-4864 is determined and then the $IC_{50}$ concentration, the concentration which inhibits 50% of the specific binding, is determined.

The $IC_{50}$ values of the most active compounds of the invention range from 1 nM to 200 nM.

The compounds of the invention are therefore ligands with an affinity for peripheral-type benzodiazepine receptors.

Study of the Neurotrophic Activity

Test of Survival of the Motor Neurons After Sectioning the Facial Nerve in Rats Aged 4 Days After lesion of the facial nerve in immature rats, the motor neurons of the facial nucleus experience neuronal death by apoptosis. Neuronal survival is evaluated using neuronal counting and histological methods.

Immature rats aged 4 days are anaesthetized with pentobarbital (3 mg/kg by the i.p. route). The right facial nerve is exposed and sectioned at its outlet from the stylomastoid foramen. After waking up, the young rats are returned to their mothers and are treated for 7 days with one or two daily administrations, by the oral or intraperitoneal route, at doses ranging from 1 to 10 mg/kg.

7 days after the lesion, the animals are decapitated and the brains are frozen in isopentane at −40° C. The entire facial nerve is cut with a cryostat into sections with a width of 10 µm. The motor neurons are stained with cresyl violet and counted using the Histo™ software (Biocom™).

In this model, the compounds of the invention increase neuronal survival by approximately 10 to 30%.

The results of the tests show that the most active compounds of the invention promote nerve regeneration.

The compounds of the invention can therefore articipate in the composition of a medicament.

They can be used for the preparation of medicaments intended for the prevention and/or treatment of various types of peripheral neuropathies, such as traumatic or ischaemic neuropathies, infectious, alcoholic, medicinal or genetic neuropathies, and motor neuron conditions, such as spinal amyotrophies and amyotrophic lateral sclerosis. These medicaments will also find an application in the treatment of neurodegenerative diseases of the central nervous system, either of acute type, such as strokes and cranial and medullar traumas, or of chronic type, such as autoimmune diseases (multiple sclerosis), Alzheimer's disease, Parkinson's disease and any other disease in which the administration of neurotrophic factors is supposed to have a therapeutic effect.

The compounds of the invention can also be used for the preparation of medicaments intended for the prevention and/or treatment of anxiety, of epilepsy and of sleep disorders. This is because ligands of the PBR or p sites stimulate the production of neurosteroids, such as pregnenolone, dehydroeplandrosterone and 3α-hydroxy-5α-pregnan-20-one, by promoting the transfer of cholesterol from the outside to the inside of the mitochondrial membrane. These neurosteroids modulate the activity of the $GABA_A$-chloride channel macromolecular complex and can thus produce anxiolytic, anticonvulsant and sedative activities (D. Bitran et al., *Psychopharmacology*, 2000, 151, 64-71; S. Okuyama et al., *Life Sci.*, 1999, 64 (16), 1455-1464; L. D. McCauley et al., *Eur. J. Pharmacol.*, 1995, 276, 145-153; S. K. Kulkarni et al., *Drugs of Today*, 1995, 31, 433-4558).

The compounds of the invention can also be used in the treatment of acute or chronic renal insufficiency, of glomerulonephritis, of diabetic nephropathy, of cardiac ischaemia and cardiac insufficiency, of myocardial infarction, of ischaemia of the lower limbs, of coronary vasospasm, of angina pectoris, of pathologies associated with the heart valves, of inflammatory heart diseases, of side effects due to cardiotoxic medicaments or as a result of heart surgery, of atherosclerosis and of its thromboembolic complications, of restenosis, of graft rejections, or of conditions related to incorrect proliferation or incorrect migration of smooth muscle cells.

Furthermore, recent data in the literature indicate that the peripheral-type benzodiazepine receptor might play a fundamental role in the regulation of cell proliferation and cancerization processes. Generally, and in comparison with normal tissues, an increased density of peripheral-type benzodiazepine receptors is observed in various types of tumors and cancers.

In human astrocytomas, the level of expression of the peripheral-type benzodiazepine receptor is correlated with the degree of malignancy of the tumor, the proliferation index and the survival of the patients. In human cerebral tumors, the increase in the number of peripheral-type benzodiazepine receptors is used as a diagnostic indication in medical imaging and as a therapeutic target for conjugates formed from a ligand of the peripheral-type benzodiazepine receptor and from a cytostatic drug. A high density of peripheral-type benzodiazepine receptors is also observed in ovarian carcinomas and breast cancers. As regards the latter, it has been demonstrated that the level of expression of the peripheral-type benzodiazepine receptors is related to the aggressive potential of the tumor; furthermore, the presence of a peripheral-type benzodiazepine receptor agonist stimulates the growth of a mammary cancer line.

These combined results, which suggest a deleterious function of the peripheral-type benzodiazepine receptor in cancerization processes, constitute a relevant basis for the search for synthetic ligands specific for the peripheral-type benzodiazepine receptor which are capable of blocking the effects thereof.

The compounds can therefore be used for the treatment of tumors and cancers.

The peripheral-type benzodiazepine receptors are also present in the skin and, in this respect, the compounds which can be used according to the invention can be used for the prophylaxis or the treatment of cutaneous stress.

The term "cutaneous stress" is understood to mean the various situations which might cause damage, in particular to the epidermis, whatever the agent which causes this stress. This agent can be internal and/or external to the body, such as a chemical or free-radical agent, or else external, such as ultraviolet radiation.

Thus, the compounds which can be used according to the invention are intended to prevent and to combat cutaneous irritation, dry patches, erythemas, dysaesthetic sensations, heating sensations, pruritus of the skin and/or mucous membranes, or ageing, and can also be used in cutaneous disorders, such as, for example, psoriasis, pruriginous diseases, herpes, photodermatoses, atopic dermatitides, contact dermatitides, lichens, prurigo, pruritus, insect stings, in fibroses and other disorders of collagen maturation, in immunological disorders or in dermatological conditions, such as eczema.

The compounds of the invention can also be used for the prevention and treatment of chronic inflammatory diseases, in particular rheumatoid arthritis, and pulmonary inflammatory diseases, in particular asthma, acute respiratory distress syndrome (ARDS) and chronic obstructive pulmonary diseases (COPD), cystic fibrosis, bronchopulmonary diseases, lung diseases or pulmonary fibrosis.

Thus, a subject-matter of the invention is pharmaceutical compositions comprising an effective dose of at least one compound of general formula (I), in the form of the base, of a pharmaceutically acceptable salt, of a pharmaceutically acceptable solvate or of a pharmaceutically acceptable hydrate, as a mixture, if appropriate, with suitable excipients.

The said excipients are chosen according to the pharmaceutical form and the method of administration desired.

The pharmaceutical compositions of the invention may thus be intended for oral, sublingual, subcutaneous, intramuscular, intravenous, topical, intratracheal, intranasal, transdermal, rectal or intraocular administration.

The unit administration forms can be, for example, tablets, gelatin capsules, granules, powders, solutions or suspensions to be taken orally or to be injected, transdermal patches or suppositories. Ointments, lotions and collyria can be envisaged for topical administration.

The said unit forms are dosed to allow a daily administration of 0.001 to 20 mg of active rinciple per kg of body weight, according to the pharmaceutical dosage form.

To prepare tablets, a pharmaceutical vehicle, which can be composed of diluents, such as, for example, lactose, microcrystalline cellulose or starch, and formulation adjuvants, such as binders (polyvinylpyrrolidone, hydroxypropylmethylcellulose, and the like), flow agents, such as silica, or lubricants, such as magnesium stearate, stearic acid, glyceryl tribehenate or sodium stearylfumarate, is added to the micronized or unmicronized active principle. Wetting or surface-active agents, such as sodium lauryl sulfate, can also be added.

The preparation techniques can be direct tableting, dry granulation, wet granulation or hot melt.

The tablets can be bare, coated with sugar, for example with sucrose, or coated with various polymers or other appropriate materials. They can be designed to make possible rapid, delayed or sustained release of the active principle by virtue of polymer matrices or of specific polymers used in the coating.

To prepare gelatin capsules, the active principle is mixed with dry pharmaceutical vehicles (simple mixing, dry or wet granulation, or hot melt) or liquid or semisolid pharmaceutical vehicles.

The gelatin capsules can be hard or soft and coated or uncoated with a thin film, so as to have a rapid, sustained or delayed activity (for example, for an enteric form).

A composition in the form of a syrup or an elixir or for administration in the form of drops can comprise the active principle in conjunction with a sweetener, preferably a calorie-free sweetener, methylparaben or propylparaben, as antiseptic, a flavor enhancer and a colorant.

The water-dispersible powders and granules can comprise the active principle as a mixture with dispersing agents or wetting agents, or dispersing agents, such as polyvinylpyrrolidone, as well as with sweeteners and flavor-correcting agents.

Recourse is had, for rectal administration, to suppositories prepared with binders which melt at the rectal temperature, for example cocoa butter or polyethylene glycols.

Use is made, for parenteral administration, of aqueous suspensions, isotonic saline solutions or sterile solutions which are injectable comprising pharmacologically compatible dispersing agents and/or wetting agents, for example propylene glycol or butylene glycol.

The active principle can also be formulated in the form of microcapsules, optionally with one or more carriers or additives, or else with a polymer matrix or with a cyclodextrin (transdermal patches or sustained release forms).

The topical compositions according to the invention comprise a medium compatible with the skin. They can be provided in particular in the form of aqueous, alcoholic or aqueous/alcoholic solutions, of gels, of water-in-oil or oil-in-water emulsions having the appearance of a cream or of a gel, of microemulsions or of aerosols or in the form of vesicular dispersions comprising ionic and/or nonionic lipids. These pharmaceutical dosage forms are prepared according to methods conventional in the fields under consideration.

What is claimed is:

1. A method for the treatment of a pathology in which the peripheral benzodiazepine receptors are involved which comprises administering to a patient in need of said treatment a therapeutically effective amount of a compound of formula (I):

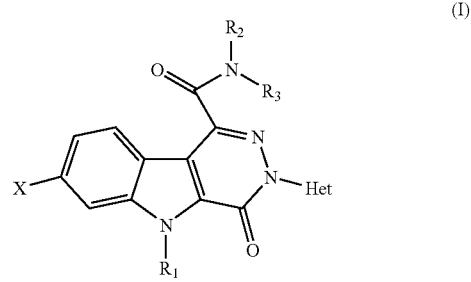

wherein

X represents a hydrogen or halogen atom, $R_1$ represents a hydrogen atom or a $(C_1\text{-}C_4)$alkyl group, $R_2$ and $R_3$ each represent, independently of one another, a hydrogen atom or a $(C_1\text{-}C_4)$alkyl group or else $R_2$ and $R_3$ form, with the nitrogen atom which carries them, a pyrrolidinyl, piperidinyl, morpholinyl or 4-alkylpiperazinyl group, and Het represents a heteroaryl group selected from pyridinyl, 1-oxidopyridinyl, quinolinyl, isoquinolinyl, pyrimidinyl, pyrazinyl and pyridazinyl, optionally substituted with one or more halogen atoms and/or one or more $(C_1-C_4)$alkyl or $(C_1-C_4)$alkoxy groups, or a hydrate or acid addition salt thereof; and wherein said pathology is selected from the group consisting of peripheral neuropathy, anxiety, epilepsy, acute or chronic renal insufficiency, glomerulonephritis, diabetic nephropathy, cardiac ischaemia and cardiac insufficiency, myocardial infarction, ischaemia of the lower limbs, coronary vasospasm, angina pectoris, graft rejection, and pulmonary inflammatory disease.

2. A method for the treatment of a pathology in which the peripheral benzodiazepine receptors are involved which comprises administering to a patient in need of said treatment a therapeutically effective amount of a compound of formula (I):

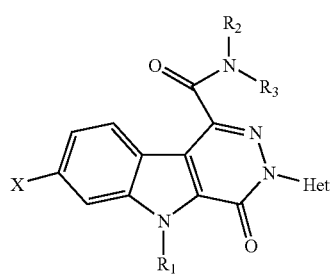

wherein

X represents a hydrogen or halogen atom, $R_1$ represents a hydrogen atom or a $(C_1-C_4)$alkyl group, $R_2$ and $R_3$ each represent, independently of one another, a hydrogen atom or a $(C_1-C_4)$alkyl group or else $R_2$ and $R_3$ form, with the nitrogen atom which carries them, a pyrrolidinyl, piperidinyl, morpholinyl or 4-alkylpiperazinyl group, and Het represents a heteroaryl group selected from pyridinyl, 1-oxidopyridinyl, quinolinyl, isoquinolinyl, pyrimidinyl, pyrazinyl and pyridazinyl, optionally substituted with one or more halogen atoms and/or one or more $(C_1-C_4)$alkyl or $(C_1-C_4)$alkoxy groups, or a hydrate or acid addition salt thereof; and wherein said pathology is selected from the group consisting of peripheral neuropathy; spinal amyotrophy; amyotrophic lateral sclerosis; anxiety; epilepsy, and diabetic nephropathy.

3. The method as set forth in claim 2 wherein

X represents a halogen atom;

$R_1$ represents a $(C_1-C_4)$alkyl;

$R_2$ and $R_3$ each represent, independently of one another, a hydrogen atom or a $(C_1-C_4)$alkyl group, or else $R_2$ and $R_3$ form, with the nitrogen atom which carries them, a pyrrolidinyl, piperidinyl, morpholinyl or 4-alkylpiperazinyl group;

Het represents a heteroaryl group selected from pyridinyl, quinolinyl, isoquinolinyl, pyrimidinyl, pyrazinyl and pyridazinyl, optionally substituted with one or more halogen atoms, and/or one or more $(C_1-C_4)$alkyl groups or $(C_1-C_4)$alkoxy groups.

4. The method as set forth in claim 2 wherein the compound is selected from the group consisting of:

7-fluoro-N,N,5-trimethyl-4-oxo-3-(pyridin-2-yl)-3,5-dihydro-4H-pyridazino[4,5-b]indole-1-carboxamide, 7-fluoro-N,N,5-trimethyl-4-oxo-3-(pyridin-3-yl)-3,5-dihydro-4H-pyridazino[4,5-b]indole-1-carboxamide, 7-fluoro-N,N,5-trimethyl-4-oxo-3-(pyridin-4-yl)-3,5-dihydro-4H-pyridazino[4,5-b]indole-1-carboxamide hydrochloride (1:1), 7-fluoro-N,N,5-trimethyl-4-oxo-3-(2-methoxypyridin-5-yl)-3,5-dihydro-4H-pyridazino[4,5-b]indole-1-carboxamide, 7-fluoro-N,N,5-trimethyl-4-oxo-3-(quinolin-3-yl)-3,5-dihydro-4H-pyridazino[4,5-b]indole-1-carboxamide, 1-[[7-fluoro-5-methyl-3-(pyrimidin-2-yl)-4-oxo-3,5-dihydro-4H-pyridazino[4,5-b]indol-1-yl]carbonyl]pyrrolidine, 4-methyl-1-[[7-fluoro-5-methyl-3-(pyridin-3-yl)-4-oxo-3,5-dihydro-4H-pyridazino[4,5-b]indol-1-yl]carbonyl]piperazine hydrochloride (1:1), 1-[[7-fluoro-5-methyl-3-(pyridin-3-yl)-4-oxo-3,5-dihydro-4H-pyridazino[4,5-b]indol-1-yl]carbonyl]pyrrolidine, 7-fluoro-N,5-dimethyl-4-oxo-3-(pyridin-3-yl)-3,5-dihydro-4H-pyridazino[4,5-b]indole-1-carboxamide, 7-fluoro-5-methyl-4-oxo-3-(pyridin-3-yl)-3,5-dihydro-4H-pyridazino[4,5-b]indole-1-carboxamide, 7-chloro-N,N,5-trimethyl-4-oxo-3-(pyridin-2-yl)-3,5-dihydro-4H-pyridazino[4,5-b]indole-1-carboxamide, 7-chloro-N,N,5-trimethyl-4-oxo-3-(pyridin-3-yl)-3,5-dihydro-4H-pyridazino[4,5-b]indole-1-carboxamide hydrochloride (1:1), 7-chloro-N,N,5-trimethyl-4-oxo-3-(pyridin-4-yl)-3,5-dihydro-4H-pyridazino[4,5-b]indole-1-carboxamide, 7-chloro-N,N,5-trimethyl-4-oxo-3-(pyridin-4-yl)-3,5-dihydro-4H-pyridazino[4,5-b]indole-1-carboxamide hydrochloride (1:1), 7-chloro-N,N,5-trimethyl-4-oxo-3-(5-methylpyridin-2-yl)-3,5-dihydro-4H-pyridazino[4,5-b]indole-1-carboxamide, 7-chloro-N,N,5-trimethyl-4-oxo-3-(2-methoxypyridin-5-yl)-3,5-dihydro-4H-pyridazino[4,5-b]indole-1-carboxamide, 7-chloro-N,N,5-trimethyl-4-oxo-3-(2-methylpyridin-5-yl)-3,5-dihydro-4H-pyridazino[4,5-b]indole-1-carboxamide, 7-chloro-N,N,5-trimethyl-4-oxo-3-(2-bromopyridin-5-yl)-3,5-dihydro-4H-pyridazino[4,5-b]indole-1-carboxamide, 7-chloro-N,N,5-trimethyl-4-oxo-3-(quinolin-3-yl)-3,5-dihydro-4H-pyridazino[4,5-b]indole-1-carboxamide, 7-chloro-N,N,5-trimethyl-4-oxo-3-(isoquinolin-4-yl)-3,5-dihydro-4H-pyridazino[4,5-b]indole-1-carboxamide, 7-chloro-N,N,5-trimethyl-4-oxo-3-(6-methylpyridazin-3-yl)-3,5-dihydro-4H-pyridazino[4,5-b]indole-1-carboxamide, 7-chloro-N,N,5-trimethyl-4-oxo-3-(pyrimidin-5-yl)-3,5-dihydro-4H-pyridazino[4,5-b]indole-1-carboxamide, 7-chloro-N,N,5-trimethyl-4-oxo-3-(pyrimidin-2-yl)-3,5-dihydro-4H-pyridazino[4,5-b]indole-1-carboxamide, 7-chloro-N,N,5-trimethyl-4-oxo-3-(pyrazin-2-yl)-3,5-dihydro-4H-pyridazino[4,5-b]indole-1-carboxamide, 1-[[7-chloro-5-methyl-3-(pyridin-3-yl)-4-oxo-3,5-dihydro-4H-pyridazino[4,5-b]indol-1-yl]carbonyl]pyrrolidine hydrochloride (1:1), 4-methyl-1-[[7-chloro-5-methyl-3-(pyridin-3-yl)-4-oxo-3,5-dihydro-4H-pyridazino[4,5-b]indol-1-yl]carbonyl]piperazine hydrochloride (1:1), 1-[[7-chloro-5-methyl-3-(pyridin-4-yl)-4-oxo-3,5-dihydro-4H-pyridazino[4,5-b]indol-1-yl]carbonyl]pyrrolidine, 7-chloro-N,5-dimethyl-4-oxo-3-(pyridin-4-yl)-3,5-dihydro-4H-pyridazino[4,5-b]indole-1-carboxamide, 7-chloro-5-methyl-4-oxo-3-(pyridin-4-yl)-3,5-dihydro-4H-pyridazino[4,5-b]indole-1-carboxamide, 7-chloro-N,N,5-trimethyl-4-oxo-3-(4-methoxypyridin-2-yl)-3,5-dihydro-4H-pyridazino[4,5-b]indole-1-carboxamide, 1-[[7-chloro-5-methyl-3-(pyridin-4-yl)-4-oxo-3,5-dihydro-4H-pyridazino[4,5-b]indol-1-yl]carbonyl]morpholine, 7-chloro-N,N,-diethyl-5-methyl-4-oxo-3-(pyridin-4-yl)-3,5-dihydro-4H-pyridazino[4,5-b]indole-1-carboxamide, 7-chloro-N-ethyl-N,5-dimethyl-4-oxo-3-(pyridin-4-yl)-3,5-dihydro-4H-pyridazino[4,5-b]indole-1-carboxamide, 1-[[7-chloro-5-methyl-3-(pyridin-4-yl)-4-oxo-3,5-dihydro-4H-pyridazino[4,5-b]indol-1-yl]carbonyl]piperidine, 7-chloro-N,N,5-trimethyl-4-oxo-3-(2-methylpyridin-4-yl)-3,5-dihydro-4H-pyridazino[4,5-b]indole-1-carboxamide, 1-[[7-chloro-5-methyl-3-(2-methylpyridin-4-yl)-4-oxo-3,5-dihydro-4H-pyridazino[4,5-b]indol-1-yl]carbonyl]pyrrolidine, 7-chloro-N,N,5-trimethyl-3-(1-oxidopyridin-4-yl)-4-oxo-3,5-dihydro-4H-pyridazino[4,5-b]indole-1-carboxamide, 7-chloro-3-(2-methoxypyridin-4-yl)-N,N,5-trimethyl-4-oxo-3,5-dihydro-4H-pyridazino[4,5-b]indole-1-carboxamide, and 3-(2-bromopyridin-4-yl)-7-chloro-N,N,5-trimethyl-4-oxo-3,5-dihydro-4H-pyridazino[4,5-b]indole-1-carboxamide, or a pharmaceutically acceptable salt or a hydrate thereof.

5. The method as set forth in claim 2 wherein the compound is selected from the group consisting of:

7-chloro-N,N,5-trimethyl-4-oxo-3-(2-methoxypyridin-5-yl)-3,5-dihydro-4H-pyridazino[4,5-b]indole-1-carboxamide, 7-chloro-N,N,5-trimethyl-4-oxo-3-(2-methylpyridin-5-yl)-3,5-dihydro-4H-pyridazino[4,5-b]indole-1-carboxamide, and 7-chloro-N,N,5-trimethyl-4-oxo-3-(2-bromopyridin-5-yl)-3,5-dihydro-4H-pyridazino[4,5-b]indole-1-carboxamide, or a pharmaceutically acceptable salt or a hydrate thereof.

6. The method as set forth in claim 2 wherein said pathology is peripheral neuropathy.

7. The method as set forth in claim 6 wherein said peripheral neuropathy is selected from the group consisting of traumatic or ischaemic neuropathy and infectious, alcoholic, medicinal or genetic neuropathy.

8. A method for the treatment of a disease comprising administering to a patient in need of said treatment a therapeutically effective amount of a compound of formula (I):

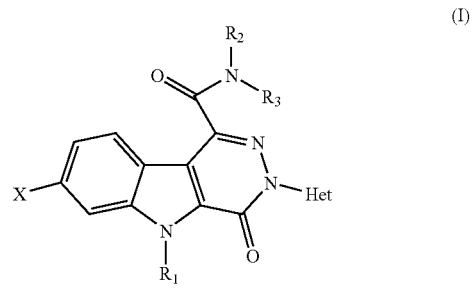

wherein

X represents a hydrogen or halogen atom, $R_1$ represents a hydrogen atom or a $(C_1-C_4)$alkyl group, $R_2$ and $R_3$ each represent, independently of one another, a hydrogen atom or a $(C_1-C_4)$alkyl group or else $R_2$ and $R_3$ form, with the nitrogen atom which carries them, a pyrrolidinyl, piperidinyl, morpholinyl or 4-alkylpiperazinyl group, and Het represents a heteroaryl group selected from pyridinyl, 1-oxidopyridinyl, quinolinyl, isoquinolinyl, pyrimidinyl, pyrazinyl and pyridazinyl, optionally substituted with one or more halogen atoms and/or one or more $(C_1-C_4)$alkyl or $(C_1-C_4)$alkoxy groups, or a hydrate or acid addition salt thereof; and wherein said disease is selected from the group consisting of peripheral neuropathy; spinal amyotrophy; amyotrophic lateral sclerosis; anxiety; epilepsy, and diabetic nephropathy.

9. The method as set forth in claim 8 wherein

X represents a halogen atom;

$R_1$ represents a $(C_1-C_4)$alkyl;

$R_2$ and $R_3$ each represent, independently of one another, a hydrogen atom or a $(C_1-C_4)$alkyl group, or else $R_2$ and $R_3$ form, with the nitrogen atom which carries them, a pyrrolidinyl, piperidinyl, morpholinyl or 4-alkylpiperazinyl group;

Het represents a heteroaryl group selected from pyridinyl, quinolinyl, isoquinolinyl, pyrimidinyl, pyrazinyl and pyridazinyl, optionally substituted with one or more halogen atoms, and/or one or more $(C_1-C_4)$alkyl groups or $(C_1-C_4)$alkoxy groups.

10. The method as set forth in claim 8 wherein the compound is selected from the group consisting of:

7-fluoro-N,N,5-trimethyl-4-oxo-3-(pyridin-2-yl)-3,5-dihydro-4H-pyridazino[4,5-b]indole-1-carboxamide, 7-fluoro-N,N,5-trimethyl-4-oxo-3-(pyridin-3-yl)-3,5-dihydro-4H-pyridazino[4,5-b]indole-1-carboxamide, 7-fluoro-N,N,5-trimethyl-4-oxo-3-(pyridin-4-yl)-3,5-dihydro-4H-pyridazino[4,5-b]indole-1-carboxamide hydrochloride (1:1), 7-fluoro-N,N,5-trimethyl-4-oxo-3-(2-methoxypyridin-5-yl)-3,5-dihydro-4H-pyridazino[4,5-b]indole-1-carboxamide, 7-fluoro-N,N,5-trimethyl-4-oxo-3-(quinolin-3-yl)-3,5-dihydro-4H-pyridazino[4,5-b]indole-1-carboxamide, 1-[[7-fluoro-5-methyl-3-(pyrimidin-2-yl)-4-oxo-3,5-dihydro-4H-pyridazino[4,5-b]indol-1-yl]carbonyl]pyrrolidine, 4-methyl-1-[[7-fluoro-5-methyl-3-(pyridin-3-yl)-4-oxo-3,5-dihydro-4H-pyridazino[4,5-b]indol-1-yl]carbonyl]piperazine hydrochloride (1:1), 1-[[7-fluoro-5-methyl-3-(pyridin-3-yl)-4-oxo-3,5-dihydro-4H-pyridazino[4,5-b]indol-1-yl]carbonyl]pyrrolidine,
7-fluoro-N,5-dimethyl-4-oxo-3-(pyridin-3-yl)-3,5-dihydro-4H-pyridazino[4,5-b]indole-1-carboxamide,
7-fluoro-5-methyl-4-oxo-3-(pyridin-3-yl)-3,5-dihydro-4H-pyridazino[4,5-b]indole-1-carboxamide,
7-chloro-N,N,5-trimethyl-4-oxo-3-(pyridin-2-yl)-3,5-dihydro-4H-pyridazino[4,5-b]indole-1-carboxamide,
7-chloro-N,N,5-trimethyl-4-oxo-3-(pyridin-3-yl)-3,5-dihydro-4H-pyridazino[4,5-b]indole-1-carboxamide hydrochloride (1:1),
7-chloro-N,N,5-trimethyl-4-oxo-3-(pyridin-4-yl)-3,5-dihydro-4H-pyridazino[4,5-b]indole-1-carboxamide,
7-chloro-N,N,5-trimethyl-4-oxo-3-(pyridin-4-yl)-3,5-dihydro-4H-pyridazino[4,5-b]indole-1-carboxamide hydrochloride (1:1),
7-chloro-N,N,5-trimethyl-4-oxo-3-(5-methylpyridin-2-yl)-3,5-dihydro-4H-pyridazino[4,5-b]indole-1-carboxamide,
7-chloro-N,N,5-trimethyl-4-oxo-3-(2-methoxypyridin-5-yl)-3,5-dihydro-4H-pyridazino[4,5-b]indole-1-carboxamide,
7-chloro-N,N,5-trimethyl-4-oxo-3-(2-methylpyridin-5-yl)-3,5-dihydro-4H-pyridazino[4,5-b]indole-1-carboxamide,
7-chloro-N,N,5-trimethyl-4-oxo-3-(2-bromopyridin-5-yl)-3,5-dihydro-4H-pyridazino[4,5-b]indole-1-carboxamide,
7-chloro-N,N,5-trimethyl-4-oxo-3-(quinolin-3-yl)-3,5-dihydro-4H-pyridazino[4,5-b]indole-1-carboxamide,
7-chloro-N,N,5-trimethyl-4-oxo-3-(isoquinolin-4-yl)-3,5-dihydro-4H-pyridazino[4,5-b]indole-1-carboxamide,
7-chloro-N,N,5-trimethyl-4-oxo-3-(6-methylpyridazin-3-yl)-3,5-dihydro-4H-pyridazino[4,5-b]indole-1-carboxamide,
7-chloro-N,N,5-trimethyl-4-oxo-3-(pyrimidin-5-yl)-3,5-dihydro-4H-pyridazino[4,5-b]indole-1-carboxamide,
7-chloro-N,N,5-trimethyl-4-oxo-3-(pyrimidin-2-yl)-3,5-dihydro-4H-pyridazino[4,5-b]indole-1-carboxamide,
7-chloro-N,N,5-trimethyl-4-oxo-3-(pyrazin-2-yl)-3,5-dihydro-4H-pyridazino[4,5-b]indole-1-carboxamide,
1-[[7-chloro-5-methyl-3-(pyridin-3-yl)-4-oxo-3,5-dihydro-4H-pyridazino[4,5-b]indol-1-yl]carbonyl]pyrrolidine hydrochloride (1:1),
4-methyl-1-[[7-chloro-5-methyl-3-(pyridin-3-yl)-4-oxo-3,5-dihydro-4H-pyridazino[4,5-b]indol-1-yl]carbonyl]piperazine hydrochloride (1:1),
1-[[7-chloro-5-methyl-3-(pyridin-4-yl)-4-oxo-3,5-dihydro-4H-pyridazino[4,5-b]indol-1-yl]carbonyl]pyrrolidine,
7-chloro-N,5-dimethyl-4-oxo-3-(pyridin-4-yl)-3,5-dihydro-4H-pyridazino[4,5-b]indole-1-carboxamide,
7-chloro-5-methyl-4-oxo-3-(pyridin-4-yl)-3,5-dihydro-4H-pyridazino[4,5-b]indole-1-carboxamide,
7-chloro-N,N,5-trimethyl-4-oxo-3-(4-methoxypyridin-2-yl)-3,5-dihydro-4H-pyridazino[4,5-b]indole-1-carboxamide,
1-[[7-chloro-5-methyl-3-(pyridin-4-yl)-4-oxo-3,5-dihydro-4H-pyridazino[4,5-b]indol-1-yl]carbonyl]morpholine,
7-chloro-N,N, diethyl-5-methyl-4-oxo-3-(pyridin-4-yl)-3,5-dihydro-4H-pyridazino[4,5-b]indole-1-carboxamide,
7-chloro-N-ethyl-N,5-dimethyl-4-oxo-3-(pyridin-4-yl)-3,5-dihydro-4H-pyridazino[4,5-b]indole-1-carboxamide,
1-[[7-chloro-5-methyl-3-(pyridin-4-yl)-4-oxo-3,5-dihydro-4H-pyridazino[4,5-b]indol-1-yl]carbonyl]piperidine,
7-chloro-N,N,5-trimethyl-4-oxo-3-(2-methylpyridin-4-yl)-3,5-dihydro-4H-pyridazino[4,5-b]indole-1-carboxamide,
1-[[7-chloro-5-methyl-3-(2-methylpyridin-4-yl)-4-oxo-3,5-dihydro-4H-pyridazino[4,5-b]indol-1-yl]carbonyl]pyrrolidine,
7-chloro-N,N,5-trimethyl-3-(1-oxidopyridin-4-yl)-4-oxo-3,5-dihydro-4H-pyridazino[4,5-b]indole-1-carboxamide,
7-chloro-3-(2-methoxypyridin-4-yl)-N,N,5-trimethyl-4-oxo-3,5-dihydro-4H-pyridazino[4,5-b]indole-1-carboxamide, and
3-(2-bromopyridin-4-yl)-7-chloro-N,N,5-trimethyl-4-oxo-3,5-dihydro-4H-pyridazino[4,5-b]indole-1-carboxamide,
or a pharmaceutically acceptable salt or a hydrate thereof.

11. The method as set forth in claim 8 wherein the compound is selected from the group consisting of:
7-chloro-N,N,5-trimethyl-4-oxo-3-(2-methoxypyridin-5-yl)-3,5-dihydro-4H-pyridazino[4,5-b]indole-1-carboxamide,
7-chloro-N,N,5-trimethyl-4-oxo-3-(2-methylpyridin-5-yl)-3,5-dihydro-4H-pyridazino[4,5-b]indole-1-carboxamide, and
7-chloro-N,N,5-trimethyl-4-oxo-3-(2-bromopyridin-5-yl)-3,5-dihydro-4H-pyridazino[4,5-b]indole-1-carboxamide,
or a pharmaceutically acceptable salt or a hydrate thereof.

12. The method as set forth in claim 8 wherein said disease is peripheral neuropathy.

13. The method as set forth in claim 12 wherein said peripheral neuropathy is selected from the group consisting of traumatic or ischaemic neuropathy and infectious, alcoholic, medicinal or genetic neuropathy.

14. The method as set forth in claim 12 wherein said peripheral neuropathy is traumatic or ischaemic neuropathy.

15. The method as set forth in claim 12 wherein said peripheral neuropathy is infectious, alcoholic, medicinal or genetic neuropathy.

16. The method as set forth in claim 12 wherein said peripheral neuropathy is infectious neuropathy.

17. The method as set forth in claim 12 wherein said peripheral neuropathy is medicinal neuropathy.

18. The method as set forth in claim 12 wherein said peripheral neuropathy is genetic neuropathy.

19. The method as set forth in claim 8 wherein said disease is diabetic nephropathy.

* * * * *

UNITED STATES PATENT AND TRADEMARK OFFICE
CERTIFICATE OF CORRECTION

PATENT NO. : 7,569,567 B2
APPLICATION NO. : 12/140608
DATED : August 4, 2009
INVENTOR(S) : Philippe Burnier et al.

It is certified that error appears in the above-identified patent and that said Letters Patent is hereby corrected as shown below:

On the Title page, in field (56), under "Other Publication", in column 2, line 1, delete "Steriods" and insert -- Steroids --, therefor.

In column 21, line 66, delete "articipate" and insert -- participate --, therefor.

In column 23, line 52, delete "rinciple" and insert -- principle --, therefor.

Signed and Sealed this

Thirteenth Day of July, 2010

David J. Kappos
*Director of the United States Patent and Trademark Office*